US00RE50788E

(19) United States
(12) Reissued Patent
Khalife et al.

(10) Patent Number: US RE50,788 E
(45) Date of Reissued Patent: Feb. 10, 2026

(54) DEVICE FOR SURGICAL INSTRUMENT, HAVING SENSORS FOR THE STORAGE OF INFORMATION

(71) Applicant: SMADE S.A.S., Lyons (FR)

(72) Inventors: Patrick Joseph Khalife, Rang du Fliers (FR); François Hassane, Merlimont (FR); Xavier Leroy, Campigneulles les Petites (FR); Laurent Pruvost, Neufchatel Hardelot (FR)

(73) Assignee: SMADE S.A.S., Lyons (FR)

(21) Appl. No.: 17/690,825

(22) Filed: Jun. 17, 2022

Related U.S. Patent Documents

Reissue of:
(64) Patent No.: 10,582,985
Issued: Mar. 10, 2020
Appl. No.: 15/707,334
Filed: Sep. 18, 2017

(30) Foreign Application Priority Data

Sep. 16, 2016 (FR) ..... 1658709

(51) Int. Cl.
*A61B 50/30* (2016.01)
*A61B 90/00* (2016.01)
*A61B 90/90* (2016.01)
*A61B 90/98* (2016.01)
*A61L 2/28* (2006.01)

(52) U.S. Cl.
CPC ..... *A61B 90/90* (2016.02); *A61B 50/30* (2016.02); *A61B 90/98* (2016.02); *A61L 2/28* (2013.01); *A61B 2050/3015* (2016.02); *A61B 2090/0803* (2016.02); *A61B 2090/0805* (2016.02);

(Continued)

(58) Field of Classification Search
CPC ..... A61B 90/90; A61B 50/30; A61B 90/98; A61B 2017/00199; A61B 2017/00734; A61B 2090/0809; A61B 2090/0813; A61B 90/06; A61L 2/24; G06K 19/07749
See application file for complete search history.

(56) References Cited

U.S. PATENT DOCUMENTS

2002/0016603 A1* 2/2002 Wells ..... B25F 5/006 606/153
2005/0046580 A1* 3/2005 Miranda-Knapp .... G08B 25/08 340/686.1

(Continued)

FOREIGN PATENT DOCUMENTS

WO WO2016/075418 A1 5/2016

OTHER PUBLICATIONS

Search Report from French Patent App. No. 1658709 dated Apr. 18, 2017.

*Primary Examiner* — Robert L Nasser
(74) *Attorney, Agent, or Firm* — Perkins Coie LLP

(57) ABSTRACT

Some embodiments are directed to a device for a surgical instrument, including at least one sensor, a circuit for controlling and processing signals coming from the at least one sensor, a memory for storing information coming from the circuit, and a radio interface for transmitting this information to an external device, the sensor(s), the circuit, the memory and the radio interface being powered by a power source, the circuit, the memory, the radio interface and the power source being housed in one or several hermetic and heat and pressure resistant case(s), in order to allow an autonomous operation of the device.

20 Claims, 2 Drawing Sheets

(52) U.S. Cl.
CPC ..... *A61B 2090/0807* (2016.02); *A61B 2562/0247* (2013.01); *A61B 2562/085* (2013.01)

(56) References Cited

U.S. PATENT DOCUMENTS

2006/0214791 A1 9/2006 Tethrake et al.
2007/0160494 A1 7/2007 Sands
2009/0267765 A1* 10/2009 Greene ..... G06K 7/0008 340/568.1
2010/0262139 A1* 10/2010 Beller ..... A61B 18/1206 606/41
2011/0034910 A1* 2/2011 Ross ..... A61B 17/068 340/5.1
2012/0165963 A1* 6/2012 Kim ..... G06F 1/266 700/22
2013/0274690 A1* 10/2013 Greenhalgh ..... A61M 11/06 604/290
2013/0314047 A1* 11/2013 Eagle ..... G06F 1/3212 320/127
2015/0088115 A1* 3/2015 Smith ..... H02J 7/00036 606/34
2015/0137972 A1* 5/2015 Nepo ..... G08B 25/016 340/539.13
2015/0272575 A1* 10/2015 Leimbach ..... A61B 90/96 227/175.3
2015/0277471 A1* 10/2015 Leimbach ..... A61B 17/068 323/299
2016/0001719 A1* 1/2016 Frost ..... B60L 53/14 307/20
2016/0249919 A1* 9/2016 Savage ..... A61B 17/072 227/175.1
2016/0287265 A1* 10/2016 Macdonald ..... A61B 90/08
2016/0347426 A1* 12/2016 Thompson ..... B63B 32/70
2017/0224400 A1* 8/2017 Mistry ..... A61B 18/00
2017/0224859 A1* 8/2017 Broninx ..... A61L 2/28
2017/0296173 A1* 10/2017 Shelton, IV ..... A61B 17/068

* cited by examiner

DEVICE FOR SURGICAL INSTRUMENT, HAVING SENSORS FOR THE STORAGE OF INFORMATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION(S)

[This application] *This is an application for reissue of U.S. Pat. No. 10,582,952, issued Mar. 10, 2020, which issued from U.S. patent application Ser. No. 15/707,334, filed Sep. 18, 2017, which* claims the priority benefit under 35 U.S.C. § 119 of French Patent Application No. 1658709, filed on Sep. 16, 2016, the contents of which are hereby incorporated in their entirety by reference.

BACKGROUND

Some embodiments relate to the field of surgical instruments. Some embodiments more specifically relate to a surgical instrument including sensors and mechanism for storing and transmitting information coming from these sensors to an external device, as well as a method of use of such a surgical instrument.

A surgical instrument is subjected during its lifespan to many stresses. These stresses can be mechanical or physical and related to their normal uses. Their natures therefore depend on the type of instruments: triggering a mechanical action, torsion, impactions, etc. Other stresses may be accidental: shocks, falls, etc. Finally, the surgical instruments are subjected to sterilizations after each use=which generates significant stresses in temperature and pressure.

These various stresses, of course, generate wear of the instrument and impact on its condition and its lifespan.

SUMMARY

It is not possible to estimate the condition of an instrument simply depending on the service life thereof, since the condition depends, on the one hand, on its effective use and on the other hand, on the type of stress that it undergoes. Furthermore, the visual examination does not allow efficiently estimating its condition either, because some types of wear are hidden: internal mechanisms, structural modification of materials, etc.

However, the use of a surgical instrument beyond a certain level of wear generates significant risks for the patient undergoing the surgical intervention.

Also, currently, in order to reduce or minimize the risk below a threshold considered as admissible, it is expected to remove the instruments from the place of use for recalibration or replacement, at a conservative periodicity, that is to say established to minimize the risks and without considering the actual degree of wear of the instrument.

These replacements and/or recalibrations have a significant cost which is incurred, depending on the case, by the manufacturer of the instrument, by its distributor or by the hospital sector.

Some embodiments reduce or minimize this cost by allowing the different stakeholders to have accurate information associated to the degree of wear of a surgical instrument. The surgical instrument may be therefore replaced or recalibrated only if necessary.

Some embodiments provide a surgical instrument addressing or overcoming the aforementioned drawbacks.

More particularly, some embodiments are directed to a device for a surgical instrument, including at least one sensor, a circuit for controlling and processing signals coming from the at least one sensor, a memory for storing information coming from the circuit, and a radio interface for transmitting the information to an external device, the at least one sensor, the circuit, the memory and the interface being powered by a power source, the circuit, the memory, the radio interface and the power source being housed in one or several hermetic, heat and pressure resistant case(s) in order to allow an autonomous operation of the device.

Some embodiments include one or more of the following features which may be used separately or in partial combination with each other or in a total combination with each other:

the case is an overmoulding made of polymeric or thermoplastic material;

wherein the radio interface is an RFID tag;

the at least one sensor includes an accelerometer and a bimetal contactor;

the radio interface is configured to receive second information from the external device in order to store it in the memory;

the sensors are configured to transmit an interrupt to the circuit, upon the occurrence of a predefined event, and wherein the circuit is adapted to keep in a standby state until receiving the interrupt and therefore to process the signals coming from the sensor corresponding to the interrupt, then to return to the standby state;

the circuit is configured to come out the standby state periodically and temporarily in order to check the consistency of the content between the memory and the internal memory thereof and the state of the power source;

the case is constituted of a material resistant to a temperature of about 135° C. and to a pressure of about 3 bar.

Some embodiments are directed to a transport box provided with a device as described above. This transport box may be adapted for the sterilization.

Some embodiments are directed to a system including a device for a surgical instrument as previously defined, and an external device provided to allow visualizing the information received from the radio interface.

According to some embodiments, this system includes one or more of the following features which may be used separately or in partial combination with each other or in total combination with each other:

the system includes a transport box provided itself with a device as previously defined;

the box contains a set of surgical instruments containing a device as previously defined.

Some embodiments are directed to a method for managing a surgical instrument including a prior step for storing information in a memory of a device associated to the instrument coming from at least one sensor embedded in the device, the memory being powered by a power source, the memory and the source being housed into at least one hermetic, heat and pressure resistant case (100) to allow an autonomous operation of the device, then a subsequent step for transmitting the information stored in the memory of the device to an external device and displaying the information on a man-machine interface of this external device.

Some embodiments are directed to a method for managing a set of surgical instruments contained in a transport box, the method including:

using the method previously described for each of the instruments of the set so that the information is transmitted to a single external device, as well as a prior step for storing information in a memory of a device associated to the box, coming from at least one sensor integrated in the device, the memory being powered by a power source, the memory and the source being housed in at least one hermetic and heat and pressure resistant case in order to allow an autonomous operation of the device, then a subsequent step for transmitting the information stored in the memory of the device to the external device, the external device allowing the display of information received from the box and the surgical instruments on a man-machine interface.

Other features and advantages of some embodiments will appear upon reading the following description, given by way of example and with reference to the appended drawings.

DETAILED DESCRIPTION OF EXEMPLARY EMBODIMENTS

Some embodiments can apply to different types of surgical instruments. For each type of instruments, different sensors may be positioned to provide information which is adapted and relevant relative to the type of wear or stress that the instrument may undergo or to follow specific features of the instrument, as well as allowing the stakeholders to judge the need to replace or to recalibrate the instrument.

Figure 1:
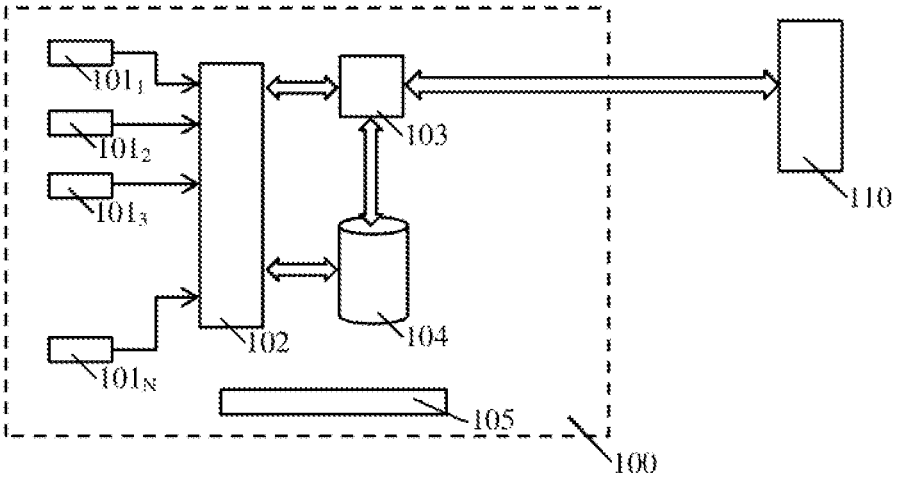
FIG. 1 schematically shows an example of a functional architecture according to an embodiment of the invention.

An example of functional architecture of a device for a surgical instrument according to the invention is illustrated in FIG. 1.

The represented functional members may be housed in a case 100 which may be located at different locations of the instrument, for example at the handle. It may be considered that some members may be located at other locations of the instrument. In this case, it may be possible to arrange several distinct cases, each protecting different members of the device.

The case 100 must meet the requirements of the sanitary standards in use in the field of application.

A surgical instrument is brought to undergo cycles of automatic and/or manual cleaning with detergent products. It may be also brought to undergo a sterilization processing after each intervention. The case must therefore be capable of protecting the members proper to the invention from this processing. Also, the case 100 must be hermetic and heat and pressure resistant.

More particularly, according to the standards currently in force, it should be constituted of a material resistant to a temperature of about 135° C. and to a pressure of about 3 bars.

Furthermore, the case may be provided to protect the members it contains from shocks, in particular shocks related to its normal operation, but also some accidental shocks such as those resulting from a fall of a worktop or a storage place (therefore typically from a height of about 1 to 2 meters).

It results therefrom that possible implementations of the case are cases not allowing to be opened. Such a possible implementation is an overmoulding made of a polymeric material, such as for example silicone, or made of a thermoplastic material, such as for example, RADEL@ R, which effectively respond to all constraints exposed above.

Within the scope of such implementations, it is therefore no longer possible to access the electronic part implementing the invention.

Consequently, some embodiments must meet lifespan constraints not lowering the lifespan of the surgical instrument itself. The different members should therefore be selected such that their estimated lifespan (or MTBF for «Mean Time Between Failure») must be at least greater than that desired for the surgical instrument (which may correspond to that of the instrument not implementing the invention).

Another constraint is the energy input for these members which should therefore come from the inside of the case itself, so that the assembly of the members it contains may operate autonomously. The case 100 may therefore contain a battery 105, dimensioned so as to allow a sufficient power supply to allow an operation of the different other members contained in the case during the desired lifespan of the surgical instrument and according to an estimated normal use of the instrument.

The arrival on the market of rechargeable batteries with «solid» substrates would allow, in a compatible volume of a surgical instrument, to face the previously described temperature and pressure conditions. This, associated to autonomous power recovery processes coming, for example, from temperature rises (during sterilizations), RFID communications or movements or vibrations of the instrument, might advantageously extend the lifespan of the electronic module of the instrument.

This same constraint influences the mechanisms implemented by the sensors and the control and processing circuit which will be explained hereinafter, in order to minimize the power consumption of the different members of the case.

The case 100 includes sensors $\mathbf{101}_1$, $\mathbf{101}_2$, $\mathbf{101}_3$, . . . $\mathbf{101}_N$, wherein N is the number of sensors. This number may possibly be equal to 1, meaning that the case includes only one single sensor.

Some embodiments are likely to be adapted to any type of sensors and therefore the sensors may be of various natures.

In particular, it may be about mechanical type sensors. An example of a mechanical sensor is a bimetal contactor, or a bimetal thermal interrupt which, depending on the temperature, opens or closes an electrical circuit accordingly allowing detecting the passage of the ambient temperature above a certain threshold.

They may be also electronic type sensors. An example of electronic sensor is an accelerometer, which may be a 3-axes accelerometer.

These sensors are preferably selected with a low power consumption as a significant criterion.

The sensors are electronically and logically connected to a control and processing circuit 102. This circuit allows controlling the sensors and processing the signals transmitted by them. In response to these signals, it may provide information which is therefore stored in a memory 104 of the EEPROM type.

The purpose of the circuit 102 is to determine the information relating to a certain number of desired measurements: these measurements may for example concern the number of times the instrument has fallen, the number of times it has undergone a sterilization, the number of times it was used, etc.

Typically, the circuit 102 therefore detects events (fall, shock, etc.), thanks to the sensors, and updates counters corresponding to the desired measurements. These desired measurements may be determined both by construction (the sensors installed in the case 100), but also, partially by programming.

The information accordingly determined by the circuit 102 is then accessible from an external device 110 by means of a radio interface 103. This radio interface may typically be a passive transmitter such as an RFID tag making the contents of the memory 104 accessible.

The access to these data by the external device 110 being advantageously supplied by the external device, via RFID technology, this access will remain possible in case of discharge or failure of the embedded source.

Figure 2:
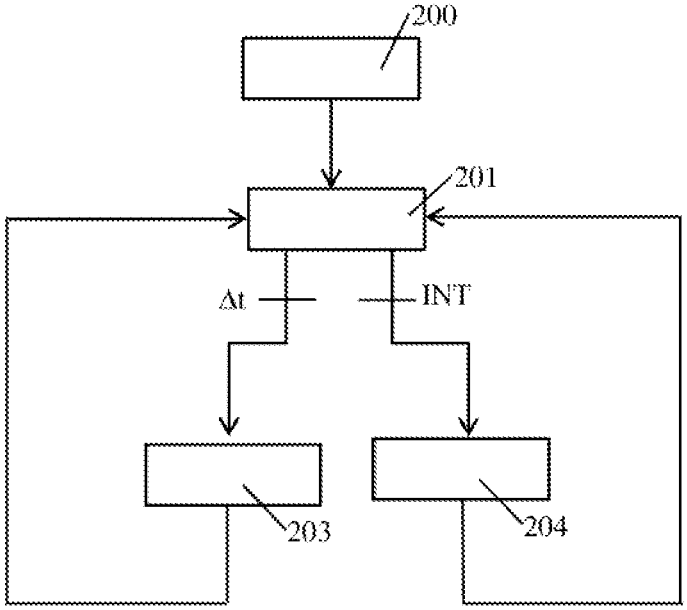
FIG. 2 schematically shows an example of a method which may be implemented by the control and processing circuit implemented in an embodiment of the invention.

The control and the processing deployed by the circuit 102 according to an implementation of the invention are shown schematically in FIG. 2.

In a first step 200, the circuit 102 controls the sensors by programming those which may be programmed.

The concerned sensors are electronic sensors, such as the accelerometers. These sensors may be configured in different ways, depending on the type of desired signal and therefore on the type of events that the circuit seeks to measure. The way of programming them may also depend on the programming capacity of the sensors.

Several situations may therefore be considered.

In a first case, the sensor may be programmed to detect a «fall» event. More specifically, this may involve programming an accelerometer in order to transmit a material interrupt intended for the circuit 102 when it detects an acceleration corresponding to a free fall during at least a predefined time (which may be adjustable).

In a second case, the sensor may not be programmed in order to determine an event type. It may be, for example, the detection of shocks, because it may be important, even determining, to understand this type of event with contextual data.

Also, the sensor can be programmed to approximately identify the event to be measured. This involves setting up an over-detection by defining an event profile rather generic. Typically for the example of the shock, this involves providing a low acceleration threshold which might correspond to a shock.

At the same time, the sensor is therefore programmed to store its values for a predefined time and according to a predefined sampling.

In the same way as previously, in the case of detecting the event, the sensor will transmit an interrupt to the circuit 102, but this time, as we will show hereinafter, the circuit will implement a more advanced processing (which is not possible to deploy on a simple sensor) in order to filter the events and avoid the over-detection.

Once the programming of the sensors is performed, the circuit 102 implements a standby step 201. This standby allows considerably reducing the overall power consumption of the members contained in the case 100, since the circuit 102 is the highest energy-consuming circuit.

This standby may be self-programmed in order to allow a standby output in two independent situations: the passage of a predefined time lapse Δt, and the reception of an interrupt coming from any of the sensors $\mathbf{101}_1$, $\mathbf{101}_2$, $\mathbf{101}_3$, . . . $\mathbf{101}_N$.

The periodic output and the deployment of the corresponding step 203 are optional and may correspond to a double verification:

The verification of the state of the power source (or battery) 105. If the power source decreases below a certain threshold, information may be stored in the memory 104 in order to indicate it to the users via the external device 110.

The verification of the consistency of the memory 104 with the internal memory of the circuit 102. A communication problem on the bus connecting the circuit 102 and the memory 104 may occur. In which case, the circuit 102 will iterate several transmissions over the bus, but in order to minimize the power consumption, after a predefined number of iterations, it may abandon but update the information in the internal memory thereof. During an next wake-up, it may thus determine an inconsistency and have a go at new writings in the memory 104.

As a result of these two verifications, the circuit 102 may return to the standby state. Thus, according to this implementation, the circuit periodically and very temporarily comes out the standby state. The processing corresponding to the two verifications is sufficiently short in order to, if the periodicity Δt is not too short, not significantly impact the lifespan of the battery 105.

Independently, the circuit 102 may come out the standby state upon receipt of an interrupt coming from one of the sensors. As has been previously seen, this may be an interrupt related to a change of state of a mechanical type sensor, or to the detection of triggering conditions by an electronic type sensor.

The circuit 102 therefore implements a processing step 204.

This processing may depend on the nature of the sensor having transmitted the interrupt and on the nature of the considered measurement.

In general, the processing consists in incrementing a counter stored in the memory 104. In this manner, the memory 104 contains the history of the surgical instrument, for example the number of times it has fallen, determined by the number of free falls detected by an accelerometer;

the number of times it has been sterilized, determined by the number of detections of a temperature above a predetermined threshold and depending on the usual sterilization temperatures;

the number of times it has been used, determined for example by a number of actuations of an appropriate sensor, or the number of detections by an appropriately configured and positioned accelerometer;

etc.

Beforehand, a post-processing may be applied to the signal transmitted by a sensor. As we have previously seen, sensors may not be programmed so as to detect all kinds of events. In this case, these are programmed in order to avoid missing an event, but to the detriment of an over-detection rate. Also, in step 204, the circuit 102 implements a finer processing allowing reducing the over-detection rate.

In particular, it may collect a set of samples captured by the sensor about the detected event and compare it to a set of signatures or templates in order to determine whether the received interrupt effectively corresponds to an actual event or whether it is an over-detection to be dismissed.

Once the interrupt is processed, the circuit may then return to the standby state (loop to step 201).

Furthermore, the case may contain a radio interface 103, in particular an RFID tag. This RFID tag allows making the contents of the memory 104 readable to external devices 110 having RFID readers (for «Radio Frequency Identification») . Other radio mechanisms are also possible (Bluetooth, etc.)

This external device may be a mobile telecommunications terminal of the «smart phone» type, a digital tablet or any other data processing equipment (desktop or laptop computer, etc.).

This external device 110 has a man-machine interface (embedded or remote) enabling a user to access the information stored in the memory 104. Thus, the hospital staff may access information allowing them to judge better the opportunity to proceed to the recalibration or the replacement of a given surgical instrument. This results in a finer management of a stock of instruments, and a reduction in costs and risks.

The distributors and the manufacturers may also access this information and may thus have metrics on the use of their instruments «in the field». They may take advantage of these data in order to adapt their commercial offers but also possibly the design of their instruments.

The radio interface 103 may be also provided to receive information from the external device 110 and to store it in the memory 104. This information may be specific to the service and/or the institution using the surgical instrument, and might thus allow following the service life of the instrument. Of course, only one part of the memory 104 may be made accessible in writing, in order to avoid erroneous or fraudulent handling of the information coming from the sensors.

It is possible to protect the access to the information stored in the memory 104 via a security mechanism. It is also possible to compartmentalize all or part of the information so that different actors (hospital staff, distributor, manufacturer . . . ) have read and/or write access, only to a predefined part of this information.

The security mechanism may be a pair user name/password which is stored in the instrument (for example in a secure system area of the memory 104) and moreover transmitted to the different actors (e-mail, postal mail, etc.)

Figure 3:
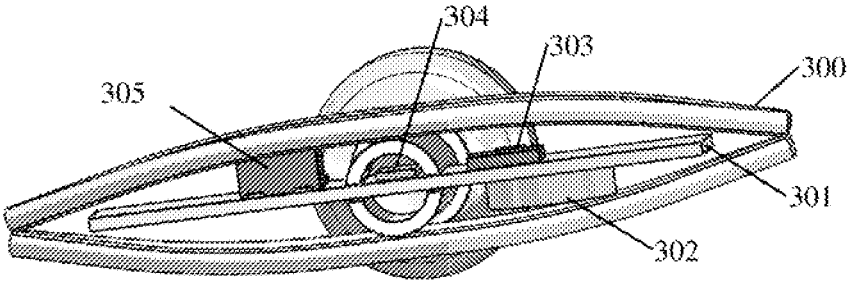
FIGS. 3 and 4 schematically show two views of an example of a handle of a surgical instrument according to an embodiment of the invention.
Figure 4:
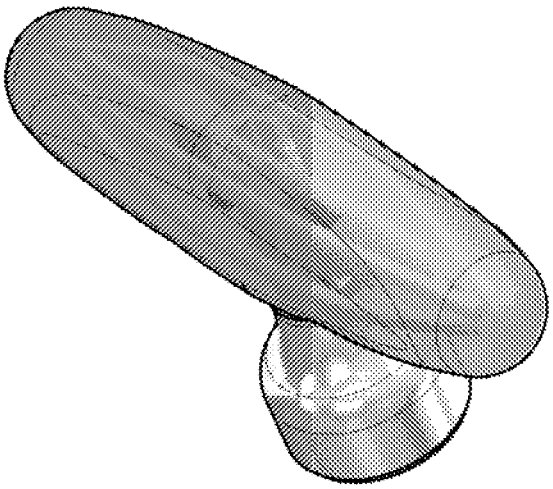

FIGS. 3 and 4 schematically show a particular surgical instrument implementing the invention. This instrument is a tool for spinal surgery. In FIGS. 3 and 4 only the handle of this instrument is represented, in which the different members of the invention are housed.

This handle includes a body 300 ensuring the holding of the members and the rigidity of the handle. This body forms a housing in which there is a base 302 receiving the different members 302, 303, 304, 305. The body 300 has therefore the additional function of protecting the members from the shocks (falls) and the gripping of the handle by the practitioner.

A battery 302, the circuit 303 are arranged on the base for controlling and processing the sensors 304, 305.

A first sensor 305 is a bimetal contactor aiming to count the number of sterilization to which the instrument is subjected.

The second sensor 304 is a 3-axis accelerometer. It allows counting the number of falls of the instrument, but also the number of triggers within the scope of a torque limiter, by the detection of a given signature.

This type of instruments for spinal surgery being both critical in terms of hazardousness for the operated patient and sensitive to the deviations of the calibration thereof, the knowledge of the information measured thanks to the invention thus allows proceeding to the recalibration or the optimal replacement thereof.

FIG. 4 represents another view of the same handle, in which the different members are housed in a case which is an overmoulding, for example made of silicone. This overmoulding is represented in the figure in a semi-transparent manner for the understanding of this embodiment of the invention.

According to some embodiments, the device may be provided to be associated to a plurality of surgical instruments. For example, the device may be located on a box dedicated to the transport and the sterilization of instrument kits. This device then includes in particular a temperature sensor (bimetal . . . ) in order to count the number of sterilization.

Thus, several surgical instruments provided with the device 100 and constituting a complete kit of ancillaries might be contained in a box (made of metal or another material) dedicated to the transport and/or the sterilization of instrument kits, itself equipped with the device 100.

Thanks to an external device 101 provided with a wide area communication RFID antenna, the data recorded in the set of the aforementioned devices (100) might be acquired substantially simultaneously by this unique external device. The box may be closed and complete, and the data acquisition may be done from a distance of more than 50 cm.

The set of retrieved data, accordingly associated to the complete kit, allowing checking the composition thereof (each instrument is indeed in the case where it was originally placed), the traceability (the kit comes out from the operating room, the cleaning/sterilization zone, the storage areas of the supplier) and the compliance (the instruments contained are one-by-one conform), will then be displayed on an external device 101 with secure access and transmitted thereby, via internet to a database available for consultation of a graphical interface, also secured.

The external device 110 may have a man-machine interface allowing the display and/or the transmission of this information, via internet, to a database available for consultation from a remote man-machine interface.

Preferably, the transmissions, the man-machine interface, the external device 110 are secure.

According to another embodiment, autonomous modules may be positioned at precise locations during the surgical operation and receive information supplied by one or several device(s) associated to surgical instruments.

Several variants are therefore possible besides those described in connection with the figures, in order to implement a device for a surgical instrument.

Thus, some embodiments are not limited to the described and represented examples and embodiments, but it is susceptible to numerous variants accessible to those of ordinary skill in the art.

The invention claimed is:

1. A device for a surgical instrument, comprising:

*at least one temperature sensor configured to determine a temperature of the device;*

*at least one acceleration sensor configured to determine information associated with movement of the device;*

[at least one sensor configured to determine information associated to a degree of wear of the surgical instrument, due to mechanical or physical stresses;]

a circuit for [controlling and] processing signals coming from the [at least one sensor] *at least one temperature sensor and the at least on acceleration sensor*;

a memory for storing information coming from the circuit;

a radio interface for transmitting *at least a portion of* the information to an external device;

a power source that powers the at least one *temperature* sensor, *the at least one acceleration sensor,* the circuit, the memory and the radio interface; *and* at least one hermetic and heat *and* pressure resistant case, the circuit, the memory, the radio interface and the power source being housed in the at least one hermetic and heat and pressure resistant case in order to allow an autonomous operation of the device, [and]

wherein the circuit is configured to periodically come out of a standby state [in order to ] *upon detection of an interruption received from the at least one acceleration sensor or the at least one temperature sensor and* check if the power source has decreased below a certain threshold.

2. The device according to claim 1, wherein the at least one *hermetic and heat and pressure resistant* case is an overmoulding made of polymeric or thermoplastic material.

3. The device according to claim 1, wherein the radio interface is an RFID tag.

4. The device according to claim 1, wherein the at least one *temperature* sensor [includes an accelerometer and] a bimetal contactor.

5. The device according to claim 1, wherein the radio interface is provided to receive second information from the external device in order to store the second information in the memory.

6. The device according to claim 1, wherein the at least one *hermetic and heat and pressure resistant* case is constituted of a material resistant to a temperature of 135° C. and to a pressure of 3 bar.

7. A transport box, comprising:

the device according to claim 1.

8. A system, comprising:

the device according to claim 1;

wherein the external device is configured to allow visualizing of the information received from the radio interface.

9. The system according to claim 8, further including a transport box.

10. The system according to claim 9, wherein the *transport* box contains a set of surgical instruments containing the device.

*11. A device for a surgical instrument, comprising:*

*at least of sensor configured to determine information associated with wear of the surgical instrument;*

*a circuit for processing signals coming from the at least on sensor;*

*a memory for at least temporarily storing information coming from the circuit;*

*a radio interface for transmitting at least a portion of the information to an external device;*

*a power source that powers the at least one sensor , the circuit, the memory and the radio interface; and*

*at least one hermetic and heat and pressure resistant case, the circuit, the memory, the radio interface and the power source being housed in the at least one hermetic and heat and pressure resistant case in order to allow an autonomous operation of the device,*

*wherein the memory comprises a counter, and the at least one sensor is configured to transmit the information to the circuit when the at least one sensor detects a mechanical or physical stress event, and the circuit is configured to increment a counter when the at least one sensor transmits the information to the circuit, and*

*wherein the circuit is configured to periodically come out of a standby state upon detection of the mechanical or physical stress event by the at least one sensor and check if the power source has decreased below a certain threshold.*

*12. The device of claim 11, wherein the radio interface is a passive transmitter.*

*13. A device for a surgical instrument, comprising:*

*at least on sensor configured to determine information associated with wear of the surgical instrument;*

*a circuit for processing signals coming from the at least on sensor;*

*a memory for at least temporarily storing information coming from the circuit;*

*a radio interface for transmitting at least a portion of the information to an external device;*

*a power source that powers the at least one sensor, the circuit, the memory and the radio interface; and*

*at least one hermetic and heat and pressure resistant case, the circuit, the memory, the radio interface and the power source being housed in the at least one hermetic and heat and pressure resistant case in order to allow an autonomous operation of the device,*

*wherein the at least one sensor is configured to transmit the information to the circuit when the at least one sensor detects a mechanical or physical stress event, and the circuit is configured to compare the information to one or more information templates to determine if the mechanical or physical stress event corresponds to a predetermined mechanical or physical stress event, and*

*wherein the circuit is configured to periodically come out of a standby state upon detection of the mechanical or physical stress event by the at least one sensor and check if the power source has decreased below a certain threshold.*

*14. The device of claim 13, wherein the radio interface is a passive transmitter.*

*15. A device for a surgical instrument, comprising:*

*at least one sensor configured to determine information associated with wear of the surgical instrument;*

*a circuit for processing signals coming from the at least one sensor;*

*a memory for storing information coming from the circuit;*

*a radio interface for transmitting at least a portion of the information to an external device;*

*a power source that powers the at least one sensor, the circuit, the memory and the radio interface; and*

*at least one hermetic and heat and pressure resistant case, the circuit, the memory, the radio interface and the power source being housed in the at least one hermetic and heat and pressure resistant case in order to allow an autonomous operation of the device,*

*wherein the circuit is configured to periodically come out of a standby state upon detection of an interruption from the at least one sensor and check if the power source has decreased below a certain threshold,*

*wherein an external device is configured to access the information stored on the memory, and*

*wherein the memory comprises a security mechanism configured to prevent access to at least a portion of the information.*

*16. The device of claim 15, wherein the radio interface is a passive transmitter.*

*17. A transport box comprising:*

*a metal housing configured to transport a plurality of surgical instruments;*

*at least one temperature sensor configured to determine information associated with a sterilization even of the plurality of surgical instruments;*

*at least one acceleration sensor configured to determine information associated with a movement event of the transport box;*

*a circuit for processing signals coming from at least one of the at least one temperature sensor or the at least one acceleration sensor;*

*a memory configured to store the information associated with the sterilization event from the at least one temperature sensor and the information associated with the movement event from the at least one acceleration sensor; and*

*a power source that powers the at least one temperature sensor, the at least one acceleration sensor, the circuit, the memory,*

*wherein the memory comprises a first counter and a second counter,*

*wherein the memory is configured to increment the first counter when the memory receives the information associated with the sterilization event from the at least one temperature sensor,*

*wherein the memory is configured to increment the second counter when the memory receives the information associated with the movement event from the at least one acceleration sensor, and*

*wherein the circuit is configured to periodically come out of a standby state upon increment of the first counter or the second counter and check if the power source has decreased below a certain threshold.*

*18. The transport box of claim 17, wherein the at least one temperature sensor comprises a bimetal contactor.*

*19. The transport box of claim 17, further comprising a radio interface, wherein the radio interface is a passive transmitter.*

*20. A device for an instrument comprising:*

*at least one temperature sensor configured to determine information associated with a temperature increase above a predetermined temperature threshold;*

*at least one acceleration sensor configured to determine information associated with movement of the device;*

*a circuit for processing signals coming from the at least one temperature sensor and the at least one acceleration sensor;*

*a memory for at least temporarily storing information coming from the circuit;*

*a radio interface for transmitting at least a portion of the information to an external device; and*

*a power source that powers the at least one temperature sensor, the at least one acceleration sensor, the circuit, the memory and the radio interface,*

*wherein the circuit is configured to periodically come out of a standby state upon determination of the temperature increase above the predetermined threshold by the at least one temperature sensor or determination of information associated with the movement of the device by the at least one acceleration sensor and check if the power source has decreased below a certain threshold, and*

*wherein the device is configured to attach to a transport box, the transport box configured to transport a plurality of medical devices.*

* * * * *